US00PP10948P

United States Patent [19]

Meilland

[11] Patent Number: Plant 10,948

[45] Date of Patent: Jun. 8, 1999

[54] HYBRID TEA ROSE PLANT NAMED 'MEINALPIR'

[75] Inventor: Alain A. Meilland, Antibes, France

[73] Assignee: CP (Delaware), Inc., Wilmington, Del.

[21] Appl. No.: 08/985,235

[22] Filed: Dec. 4, 1997

[51] Int. Cl.[6] ..... A01H 5/00

[52] U.S. Cl. ..... Plt./131

[58] Field of Search ..... Plt./11, 12, 130, Plt./131

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which forms attractive blossoms that are smoked red on the inner surface and cream with tones of silver on the outer surface. Such blossoms posses no fragrance. The plant exhibits an erect growth habit, broad decorative dark green and semi-glossy foliage, and good disease resistance. The new variety is particularly well suited for producing cut flowers under greenhouse growing conditions.

2 Drawing Sheets

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the cross of the 'Meikola' variety (U.S. Plant Pat. No. 5,607) and the 'Jelpirofor' variety (U.S. Plant Pat. No. 5,632). The male parent (i.e., the pollen parent) was the 'Meibiranda' variety (U.S. Plant Pat. No. 4,705). The parentage of the new variety can be summarized as follows:

('Meikola'×'Jelpirofor')×('Meibiranda').

The seeds resulting from the above pollination were sown and small plants were obtained which were physically and biologically different from each other. Selective study resulted in the identification of a single plant of the new variety. It was found that the new variety of Hybrid Tea rose plant of the present invention possesses the following combination of characteristics:

(a) forms attractive blossoms that are smoked red on the inner surface and cream with tones of silver on the outer surface,
(b) exhibits an erect growth habit,
(c) forms decorative broad foliage that is dark green and semi-glossy,
(d) exhibits good disease resistance with respect to Downey Mildew and Botrytis, and
(e) is particularly well suited for the production of cut flowers under greenhouse growing conditions.

The blossoms are "smoked" in the sense that bluish shades are present with the red coloration and convey an overall red-purple coloration. The blossoms exhibit more of the bluish shades upon maturation as oxidation progresses. The "silver" tones convey a slightly metallic impression to the appearance of the blossoms.

The new variety well meets the needs of the horticultural industry and exhibits good productivity during cut flower production in a greenhouse.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meinalpir' variety.

BRIEF DESCRIPTION OF THE PHOTOGRAPHS

The accompanying photographs shows as nearly true as it is reasonably possible to make the same, in a color illustration of this character, typical specimens of the plant parts of the new variety. The rose plants of the new variety were two years of age and were observed during March while budded on *Rosa indica* understock and growing in greenhouses at Le Cannet des Maures, Var, France. Dimensions in centimeters are indicated at the bottom of the photograph. Page 61 from The R.H.S. Colour Chart of The Royal Horticultural Society is shown at the lower-left portion of the photograph for comparative purposes. It has not always been possible to photographically illustrate the colors with complete accuracy. For instance, the petals as shown in the photographs sometimes appear to lack the purple-red coloration and appear to be merely deep red in coloration.

FIG. 1 illustrates a specimen of a young shoot;

Figures 2, 3, 4, 5, 6, 7, 8, 9, 10, 11, 12, 13, 14, 15, 16:
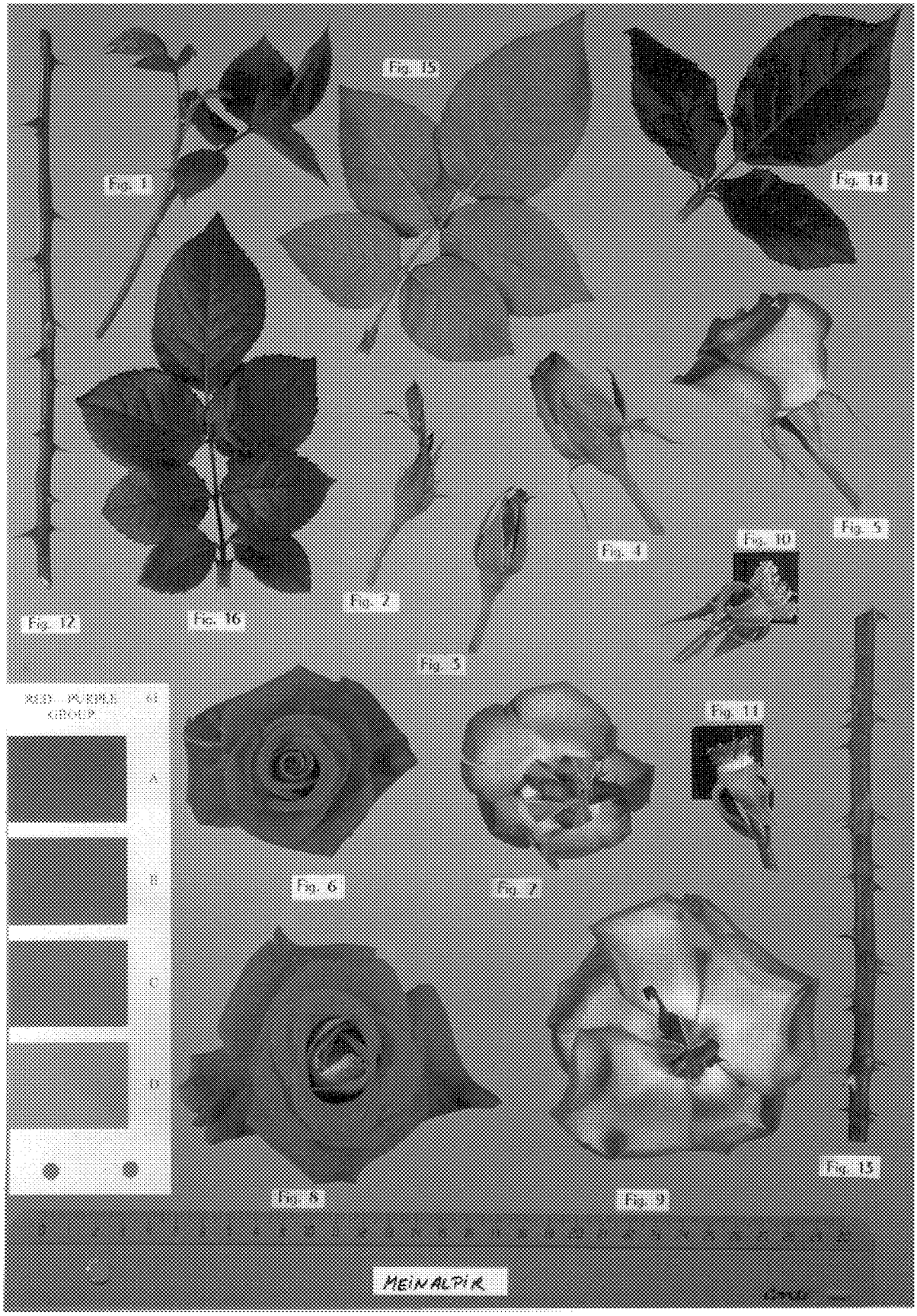
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of ths pistils (stamens removed)
FIG. 12 illustrates a specimen of a flowering stem.
FIG. 13 illustrates a specimen of main branch.
FIG. 14 illustrates a specimen of a leaf with three leaflets — plan view — upper surface.
FIG. 15 illustrates a specimen of a leaf with five leaflets — plan view — under surface.
FIG. 16 illustrates a specimen of a leaf with seven leaflets — plan view — upper surface.
Figure 17:
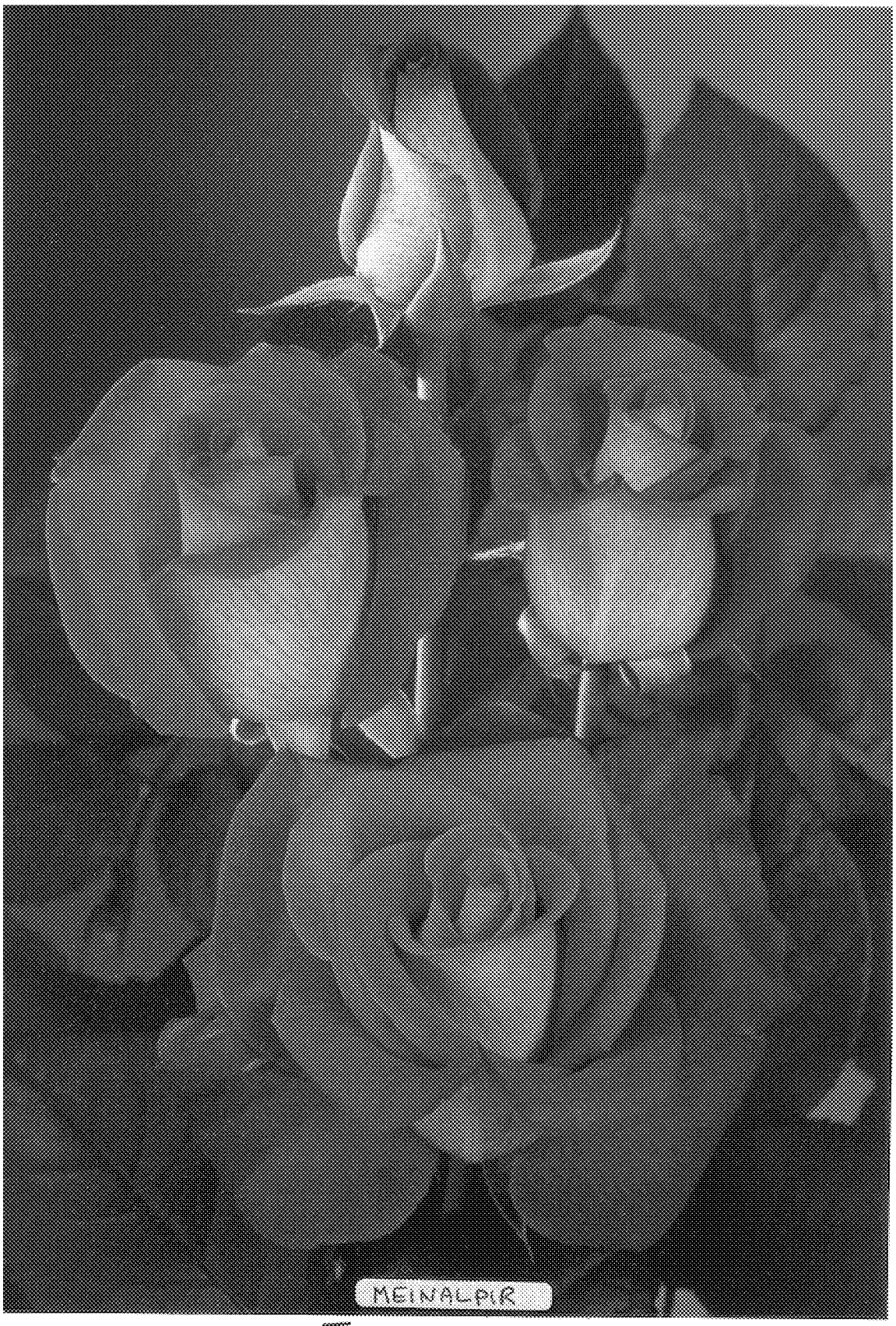

Additionally, provided as FIG. 17 is a photograph that illustrates typical blossoms and foliage of the new variety. It has proven to be impossible to depict the blossom coloration with complete accuracy in all instances. However, the true purple-red blossom coloration is shown to some degree on the outer petals of the fully open blossom at the bottom of the photograph.

DETAILED DESCRIPTION

The chart used in the identification of the colors is that of The Royal Horticultural Society (R.H.S. Colour Chart). The description is based on the observation of one and one-half year-old plants during November while budded on *Rosa indica* understock and growing indoors at Le Cannet des Maures, Var, France. The coloration in common terms precedes reference to the chart in some instances.

Class: Hybrid Tea.

Plant:

*Height.*—When pruned to a height of 85 cm., floral stems of approximately 50 to 70 cm. in length commonly are produced.

*Habit.*—Erect.

Branches:

*Color.*—Young stems: near Yellow-Green Group 144B and widely suffused with reddish coloration. Adult wood: near Yellow-Green Group 147B.

*Thorns.*—Size: medium (as illustrated). Quantity: numerous. Color: brownish to reddish brown, Greyed-Orange Group 176B on young wood, and Greyed-Orange Group 175A and 175B on adult wood.

Leaves:

*Stipules.*—Adnate, pectinate, broad and linear and Yellow-Green Group 147A in coloration.

*Petioles.*—Upper surface: Yellow-Green Group 146D in coloration and more or less glandular in nature. Under surface: light green, Yellow-Green Group 146C and bear some small thorns.

*Leaflets.*—Number: 3, 5 (most often), and 7. Shape: oval and broad. Size: medium. Serration: regular (as illustrated). Texture: consistent. General appearance: dense, medium green, and semi-glossy. Color (young foliage): Upper syrface: near Green Group 138A, and widely suffused with reddish coloration. Under surface: near Yellow-Green Group 147C. Color (adult foliage): Upper surface: dark green, near Green Group 139A. Under surface: light green, near Green Group 138A.

Inflorescence:

*Number of flowers.*—Usually one flower per stem.

*Peduncle.*—Light green, near Yellow-Green Group 146B in coloration, and the length is approximately 12 cm. on average.

*Sepals.*—Upper surface: tomentose and greenish Yellow-Green Group 146B in coloration. Under surface: light green in coloration and commonly with some extensions (as illustrated).

*Buds.*—Shape: conical. Size: large. Length: approximately 3 to 4 cm. on average. Color upon opening: Upper surface: near Red-Purple Group 61A. Under surface: near Red-Purple Group 61D and widely suffused with Red-Purple Group 61B and bordered with Red-Purple Group 61A.

*Flower.*—Shape: cupped with substantially parallel sides. Diameter: commonly approximately 10 to 13 cm. on average. Color (when opening begins): Upper surface: near Red-Purple Group 61A. Under surface: near Red-Purple Group 61D and suffused with Red-Purple Group 61B and bordered with Red-Purple Group 61A. Color (when blooming): Uper surface: near Red-Purple Group 61A. Under surface: near Red-Purple Group 61D and suffused with Red-Purple Group 61B and bordered with Red-Purple Group 61A. Color (at end of opening): Upper surface: near Red-Purple Group 61A. Under surface: near Red-Purple Group 61D and suffused with Red-Purple Group 61B and bordered with Red-Purple Group 61A. Fragrance: none. Lasting quality: approximately 6 to 8 days on the plant and approximately 8 to 10 days when cut and placed in a vase. Petal number: commonly approximately 20 to 25 on average. Petal shape: rounded with reflexed edges. Petal drop: The petals commonly detach cleanly. Stamen number: approximately 100 on average. Anthers: canary yellow in coloration. Filaments: pinkish in coloration. Pistils: approximately 135 to 140 on average. Stigmas: substantially white in coloration. Styles: reddish in coloration. Receptacle: light green, Yellow Green Group 146C in coloration, smooth, and in longitudinal section in the shape of a pear. Hips: are formed following artificial pollination.

Development:

*Vegetation.*—Vigorous.

*Blooming.*—Abundant, and commonly produces 140 to 160 flowers/m.$^2$/year.

*Resistance to disease.*—Good with respect to Downey Mildew and Botrytis.

I claim:

1. A new and distinct variety of Hybrid Tea rose plant characterized by the following combination of characteristics:

(a) forms attractive blossoms that are smoked red on the inner surface and cream with tones of silver on the outer surface,
(b) exhibits an erect growth habit,
(c) forms decorative broad foliage that is dark green and semi-glossy,
(d) exhibits good disease resistance with respect to Downey Mildew and Botrytis, and
(e) is particularly well suited for the production of cut flowers under greenhouse growing conditions;

substantially as herein shown and described.

* * * * *

RED - PURPLE GROUP
A
B
C
D

MEINALPIK